(12) United States Patent
Doyle et al.

(10) Patent No.: US 6,608,199 B2
(45) Date of Patent: Aug. 19, 2003

(54) SYNTHESIS OF CHLORINATED PYRIMIDINES

(75) Inventors: Timothy John Doyle, Bucks, AL (US); Alan Henry Benke, Bucks, AL (US); Peter Karl Wehrenberg, Bucks, AL (US); Louie Akos Nady, Bucks, AL (US)

(73) Assignee: Syngenta Limited (GB)

( * ) Notice: Subject to any disclaimer, the term of this patent is extended or adjusted under 35 U.S.C. 154(b) by 0 days.

(21) Appl. No.: 09/876,964

(22) Filed: Jun. 8, 2001

(65) Prior Publication Data

US 2002/0055633 A1 May 9, 2002

Related U.S. Application Data

(60) Provisional application No. 60/216,882, filed on Jul. 7, 2000.

(51) Int. Cl.$^7$ ............... C07D 239/20; C07C 249/00
(52) U.S. Cl. ............... 544/319; 544/242; 544/344; 564/278
(58) Field of Search ............... 544/242, 319, 544/334; 564/278

(56) References Cited

U.S. PATENT DOCUMENTS

| | | | | |
|---|---|---|---|---|
| 4,353,830 A | * | 10/1982 | Mark | 548/558 |
| 4,668,788 A | | 5/1987 | Beitzke et al. | 544/319 |
| 5,145,856 A | | 9/1992 | Clough et al. | 514/274 |
| 5,583,226 A | | 12/1996 | Stucky et al. | 544/322 |
| 5,677,453 A | | 10/1997 | Cramm et al. | 544/334 |
| 5,723,612 A | | 3/1998 | Huber et al. | 544/334 |
| 5,750,694 A | | 5/1998 | Jones et al. | 544/334 |
| 6,018,045 A | | 1/2000 | Whitton et al. | 544/334 |
| 6,096,892 A | | 8/2000 | Crombie et al. | 544/319 |
| 6,160,117 A | | 12/2000 | Whitton et al. | 544/319 |

FOREIGN PATENT DOCUMENTS

| | | |
|---|---|---|
| GB | 2287466 | 9/1995 |
| WO | 0 095 637 | 5/1983 |
| WO | 92/08703 | 5/1992 |
| WO | 95/29166 | 11/1995 |

OTHER PUBLICATIONS

Research Disclosure 39104 (1996), Anonymous.
Kenner et al., *J. Chem. Soc.*, 574 (1943).
Hull, *J. Chem. Soc.*, 2214 (1951).
Yanagida et al., *J. Org. Chem.* 34(10):2972–2975 (1969).
Yanagida et al., J. Bull. Chem. Soc. (46):299–302 (1973).

* cited by examiner

*Primary Examiner*—John M. Ford
*Assistant Examiner*—Tamthom N. Truong
(74) *Attorney, Agent, or Firm*—Rose M. Allen

(57) ABSTRACT

The invention provides a process for synthesizing chlorinated pyrimidines. The process includes reacting imidoyl chloride compounds with phosgene ($COCl_2$). The imidoyl chloride compounds can be supplied as starting materials or can be produced by reacting organic amides with phosgene or reacting organic nitrites with hydrogen chloride. The chlorinated pyrimidines, such as 4,6-dichloropyrimidine, can be used to synthesize other compounds useful in a variety of compositions, such as fungicides, pesticides, and pharmaceuticals.

26 Claims, 2 Drawing Sheets

4,6-dichloropyrimidine 4-chloro-6-hydroxypyrimidine 5-substituted-4,6-dichloropyrimidines 5-substituted-4-chloro-6-hydroxypyrimidine

SYNTHESIS OF CHLORINATED PYRIMIDINES

This application claims the benefit of provisional application Ser. No. 60/216,882 Jul. 7, 2000.

FIELD OF THE INVENTION

This invention relates to the field of organic compounds. More particularly, this invention relates to the synthesis of certain chlorinated pyrimidines such as 4,6-dichloropyrimidine. In general, synthesis of chlorinated pyrimidines according to the present invention is accomplished by reacting imidoyl chlorides with phosgene.

DESCRIPTION OF RELATED ART

Chlorinated pyrimidines prepared by the process of the present invention and, in particular 4,6-dichloropyrimidine, are known as useful compounds in the synthesis of many biologically active compounds. Use of such chlorinated pyrimidines in production of such varied compositions as pesticides and pharmaceuticals makes them economically important compounds as well. For example, 4,6-dichloropyrimidine can be used in the manufacture of azoxystrobin, a methoxyacrylate-type fungicide. Because of their wide use and economic importance, many methods of synthesis of chlorinated pyrimidines, especially 4,6-dichloropyrimidine, have been developed.

For example, U.S. Pat. No. 6,018,045 to Whitton et al. discloses a process for preparing 4,6-dichloropyrimidine that comprises treating 4,6-dihydroxyprimidine with phosphorous oxychloride (phosphoryl chloride) in the presence of a saturated hindered amine, the hydrochloride salt of a saturated hindered amine, or an unsaturated 5-membered nitrogen containing ring, or a mixture thereof. As a further step, the 4,6-dichloro-pyrimidine formed from these reactions is first directly extracted by, for example, a countercurrent liquid—liquid separation technique. The process may also include mixing the residue that remains after the direct extraction with an aqueous solution of sodium or potassium hydroxide in order to liberate the saturated hindered amine or unsaturated 5-member nitrogen-containing ring (or mixture thereof), that was used in the process.

Other disclosures generally relating to preparation of 4,6-dichloropyrimidine by reacting 4,6-dihydroxypyrimidine with phosphorous oxychloride in the presence of a suitable base include Kenner et al. (J. CHEM. SOC., November 1943, pp. 574–575), Hull (J. CHEM. SOC., August 1951, p. 2214), British Patent GB2287466, and U.S. Pat. No. 5,583,226 to Stucky et al. In addition, U.S. Pat. No. 5,677,453 to Cramm et al. discloses synthesis of 4,6-dichloropyrimidines by reacting 4,6-dihydroxypyrimidines with excess phosphoryl chloride. In this type of synthesis, no base is added; however, an excess of phosphorus and chloride is used (with respect to the 4,6-dihydroxyprimidines). This excess is maintained by adding phosphorus trichloride and chlorine to the reaction mixture in amounts such that the phosphorus trichloride is maintained in excess over the chlorine. The process is carried out at temperatures of 60–110° C. Distillation is advantageously used to purify the 4,6-dichloropyrimidines. Further, U.S. Pat. No. 5,750,694 to Jones et al. and WO 95/29166 (Zeneca Limited) disclose that 4,6-dichloropyrimidine can be prepared by reacting 4,6-dihydroxypyrimidine with phosgene (carbonyl chloride; carbon oxychloride; $COCl_2$) in the presence of a suitable base. The base is preferably a tertiary amine and the base-to-phosgene ratio is preferably in the range of 10:1 to 1:10. Preferably, the process is carried out in a solvent or a mixture of solvents, with chlorinated solvents, ethers, and polar aprotic solvents being preferred.

Yanagida et al. (J. ORG. CHEM. 34(10):2972–2975, 1969) disclose preparation of specific 2,5-disubstituted-4,6-dichloropyrimidines by reacting an aliphatic nitrile compound of the general formula $RCH_2CN$ with itself in the presence of HCl and $COCl_2$. According to the synthesis of Yanagida et al., R can be H, $CH_3$, $CH_3CH_2$, $CH_3(CH_2)_2$, $CH_2(CH_2)_3$, $(CH_3)_2CH$, Cl, $Cl(CH_2)_2$, or $CH_3CH_2O(CH_2)_2$. The authors propose a reaction scheme in which 2,5-disubstituted-4,6-dichloropyrimidine synthesis proceeds through a 6-chloro-2,5-disubstituted-4(3H)pyrimidone intermediate. Further reaction of these intermediates with phosgene gives the corresponding 2,5-disubstituted-4,6-dichloropyrimidines. The authors also propose a second reaction scheme for formation of 2,5-disubstituted-4,6-dichloropyrimidines from aliphatic nitrites. In the second scheme an aliphatic nitrile condenses with itself in the presence of HCl to form an amidine, which is then converted in the presence of phosgene to ultimately give a 2,5-disubstituted-4,6-dichloropyrimidine. Further, Yanagida et al. (J. BULL. CHEM. SOC. JAPAN 46:299–302, 1973) discloses reaction of N-(α-chloroalkenyl)alkylamidine hydrochlorides with phosgene to create 4,6-dichloro-2,5-disubstituted pyrimidines.

However, none of these references disclose the preparation of chlorinated pyrimidines that are not substituted in the 2 position, including 4,6-dichloropyrimidine itself. Synthesis of chlorinated pyrimidines that are not substituted in the 2-position requires cross-condensation of two distinct imidoyl chloride compounds, with one of the imidoyl chloride components being derived from either hydrogen cyanide or formamide.

Because of the economic importance of 4,6-dichloropyrimidine in the production of agricultural and medical compounds, as well as its importance in production of tools for scientific research, new, straightforward, rapid, and cost-effective methods for synthesis of this chlorinated pyrimidine are continually being developed.

SUMMARY OF THE INVENTION

The present invention provides a method of synthesizing 4,6-dichloropyrimidine, 4-chloro-6-hydroxypyrimidine, 5-substituted-4-chloro-6-hydoxypyrimidines, and 5-substituted-4,6-dichloropyrimidines. The method is less expensive and simpler than those methods currently available. In general, the method of preparing these compounds according to the present invention comprises cross-condensation of formamidoyl chloride with a distinct imidoyl chloride compound in the presence of phosgene ($COCl_2$) and HCl and, optionally, in the presence of solvent. For present purposes, "distinct imidoyl chloride compound" refers to compounds with different hydrocarbyl groups, preferably different alkyl groups, than formamidoyl chloride, for example, acetamidoyl chloride. The present invention also includes use of compounds which can be easily converted into imidoyl chlorides under reaction conditions, for example, nitriles like acetonitrile which react with HCl to give the imidoyl chloride. In the case of formamidoyl chloride, the starting materials can optionally be HCN and HCl; or formamide and $COCl_2$.

In one embodiment, the synthesis method of the present invention includes cross-condensation of imidoyl chloride compounds derived from a nitrile and hydrogen cyanide. For example, the method of the invention can include reacting acetonitrile and hydrogen cyanide with hydrogen chloride and phosgene to form 4,6-dichloropyrimidine.

In other embodiments of the invention, the method includes cross-condensation of imidoyl chloride compounds derived from an alkylamide and hydrogen cyanide. For example, the method of the invention can include reacting acetamide and hydrogen cyanide with hydrogen chloride and phosgene to form 4,6-dichloropyrimidine.

In further embodiments of the invention, the method includes cross-condensation of imidoyl chloride compounds derived from a nitrile and formamide. For example, the method of the invention can include reacting acetonitrile and formamide with hydrogen chloride and phosgene to form 4,6-dichloropyrimidine.

In other embodiments of the invention, the method includes cross-condensation of imidoyl chloride compounds derived from an alkylamide and formamide. For example, the method of the invention can include reacting acetamide and formamide with hydrogen chloride and phosgene to form 4,6-dichloropyrimidine.

The solvent can optionally be an inert organic solvent, for example chlorobenzene, or an excess of one of the raw materials, for example acetonitrile.

Reaction temperatures can be in the range of 0° C. to 160° C., preferably 60° C. to 120° C., and most preferably 100° C. to 110° C.

The reaction is typically carried out in a sealed vessel under autogenous pressure of 0 to 800 psig, preferably 100 to 300 psig, and most preferably 150 to 250 psig.

The process of the invention results in preferential formation of the desired chlorinated pyrimidine (i.e., the cross condensation product) relative to formation of the chlorinated pyrimidine substituted at the 2 position (i.e., the self condensation product). In particular, it is surprising to observe that reaction of formamidoyl chloride or its equivalents with acetamidoyl chloride or its equivalents favors the production of 4,6-dichloropyrimidine, the cross-coupling product, over the production of 2-methyl-4,6-dichloropyrimidine, the self condensation product from acetonitrile. For example, an equimolar mixture of the two (formamidoyl chloride or equivalent with acetamidoyl chloride or equivalent) is expected to give the statistical 1:1 distribution of 4,6-dichloropyrimidine and 2-methyl-4,6-dichloropyrimidine. In contrast a distribution of approximately 10:1 is typically observed favoring 4,6-dichloropyrimidine itself. Similarly, when a large excess of acetonitrile relative to formamidoyl chloride is used, the product ratio indicates that the cross-condensation product is preferentially formed. For example, when a 37:1 molar ratio of acetonitrile to formamidoyl chloride is used, the ratio of 4,6-dichloropyrimidine to 2-methyl-4,6-dichloropyrimidine is approximately 1:1.4. In a statistical distribution of products, a ratio of 1:37 would be expected.

All of the embodiments described above can also be used for the preparation of 4-chloro-6-hydroxypyrimidine by limiting the amount of phosgene or by conducting the reaction at low temperatures.

All of the embodiments described above can also be used for the preparation of certain 5-substituted-4,6-dichloropyrimidines by using appropriately substituted amides or nitriles. For example, the method of the invention can include reacting butyronitrile and formamide with hydrogen chloride and phosgene to form 5-ethyl-4,6-dichloropyrimidine.

All of the embodiments described above can also be used for the preparation of 5-substituted-4-chloro-6-hydroxypyrimidine by using appropriately substituted amides or nitrites and by limiting the amount of phosgene or by conducting the reaction at low temperatures.

The chlorinated pyrimidines produced by the method of the invention can be used to synthesize commercially or medically important compounds. For example, the chlorinated pyrimidines, especially 4,6-dichloropyrimidine, can be used to make pesticides, and/or pharmaceuticals, such as nucleoside analogs and compounds that are active on the central nervous system (CNS) of animals and humans.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

DETAILED DESCRIPTION

Reference will now be made in detail to the preferred embodiments of the present invention. While the following detailed description relates to preferred embodiments of the invention, the invention is not limited in scope to the specific details provided below, but encompasses the entire scope disclosed and claimed herein, including all obvious variations that can be made by those skilled in the art.

Figure 1:
FIG. 1 depicts the chemical structures of 4,6-dichloropyrimidine, 4-chloro-6-hydroxypyrimidine, 5-substituted-4,6-dichloropyrimidines, and 5-substituted-4-chloro-6-hydroxypyrimidines.
Figure 1:
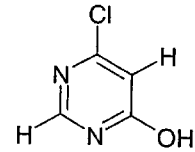
Figure 1:
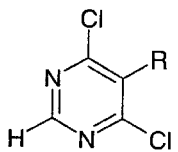
Figure 1:
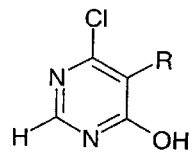

The present invention relates to methods of synthesizing 4,6-dichloropyrimidine, 4-chloro-6-hydroxypyrimidine, 5-substituted-4,6-dichlorpyrimidines, and 5-substituted-4-chloro-6-hydroxypyrimidines from imidoyl chloride compounds. The present invention contemplates use of starting materials that can be converted to imidoyl chlorides in situ under reaction conditions. Such starting materials include mixtures of nitriles and HCl, as well as mixtures of amides and phosgene. FIG. 1 shows the chemical structures of 4,6-dichloropyrimidine, 4-chloro-6-hydroxypyrimidine, 5-substituted-4,6-dichlorpyrimidines, and 5-substituted-4-chloro-6-hydroxypyrimidines. The methods of synthesizing these compounds comprise reacting phosgene ($COCl_2$) with imidoyl chloride compounds of the formula:

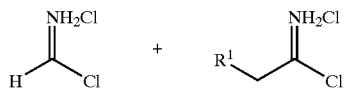

in which $R^1$ can be, independently, hydrogen or a $C_1$–$C_{12}$ hydrocarbyl group, and at least one of the imidoyl chlorides must have two alpha hydrogens. In the case where a 5-substituted-4,6-dichlorpyrimidine or a 5-substituted-4-chloro-6-hydroxypyrimidine is formed, the 5 substituent is the same moiety as the $R^1$ moiety of the above imidoyl chloride. The term $C_1$–$C_{12}$ "hydrocarbyl group" refers to hydrocarbyl groups such as alkyl, alkenyl, alkynyl, alkoxy, aryl, and the like wherein said hydrocarbyl group is optionally substituted with 1–5 (preferably 1 or 2) substituents. The substituents of the aliphatic moieties can be halo, aryl, alkoxy or the like, and the substituents of the aromatic moieties can be halo, alkyl, alkoxy, alkenyl, alkynyl, or the like. Preferred are $C_1$–$C_6$ hydrocarbyl groups such as phenyl and lower alkyl, and more preferred are $C_1$–$C_3$ hydrocarbyl groups, particularly alkyl groups such as methyl, ethyl, propyl or isopropyl. The imidoyl chlorides can be prepared in situ by the reaction of a nitrile with HCl, or by the reaction of an amide with phosgene.

Figure 2:
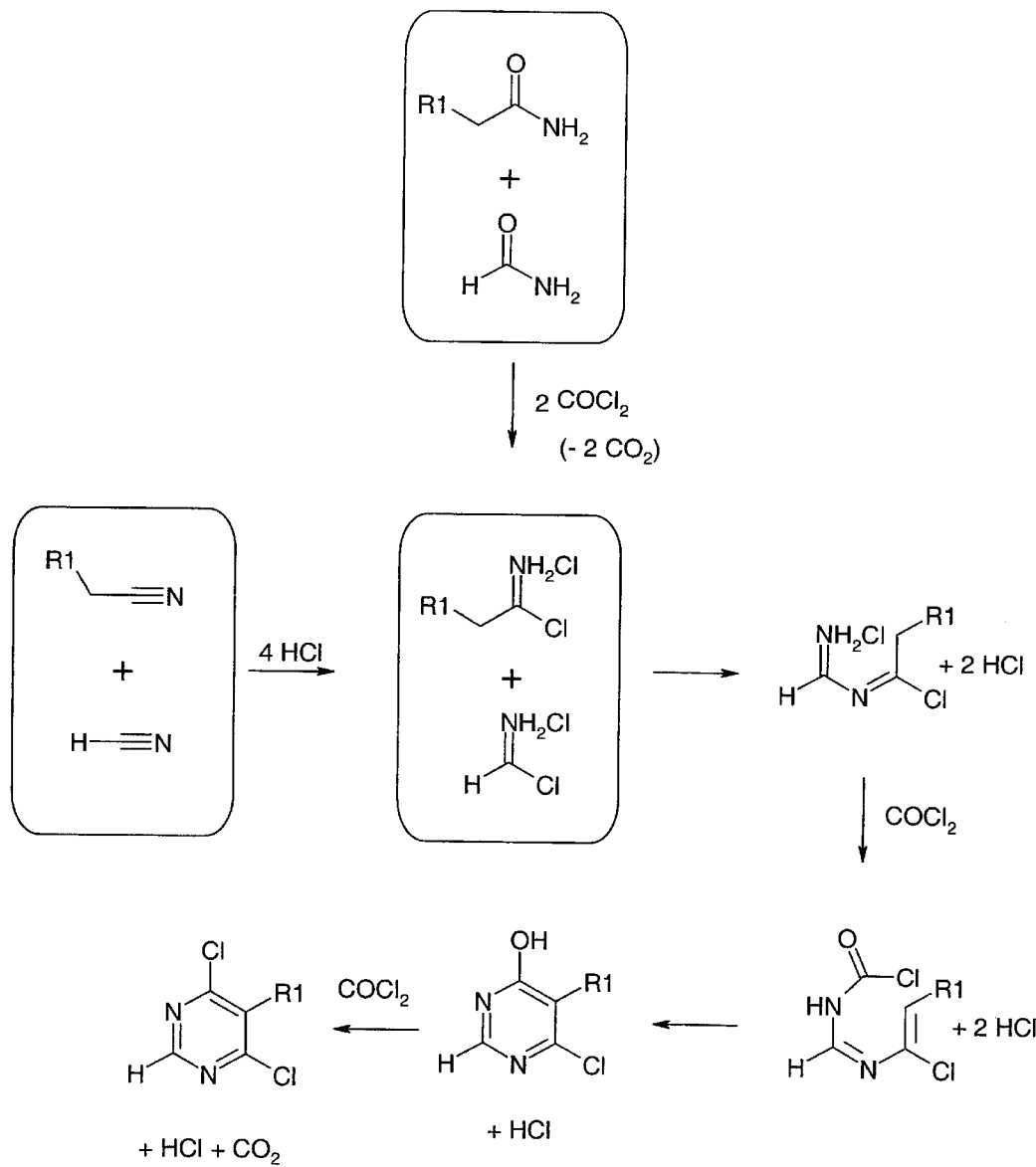
FIG. 2 depicts a general mechanism that accounts for synthesis of 4-chloro-6-hydroxypyrimidines and 4,6-dichloropyrimidines according to the invention.

In the method of synthesis of chlorinated pyrimidines according to the present invention, two distinct imidoyl chloride compounds are reacted with phosgene to synthesize the desired chlorinated pyrimidine. One or both of the imidoyl chloride compounds can be supplied pre-formed to the method of synthesizing chlorinated pyrimidines according to the invention. Alternatively, both of the imidoyl chloride compounds can be synthesized as part of the method of synthesis of chlorinated pyrimidines according to the invention. For example, one or both of the imidoyl chloride compounds can be synthesized from organic amides or from organic nitrites. In one embodiment of the present invention, one imidoyl chloride compound is synthesized from an organic amide while the other imidoyl chloride is synthesized from an organic nitrile. A general reaction scheme that includes the optional formation of imidoyl chloride intermediates from both organic amides (e.g., formamide and acetamide) and organic nitrites (e.g., hydrogen cyanide and acetonitrile) is presented in FIG. 2. As depicted in FIG. 2, cross-condensation of two different imidoyl chloride compounds can produce an intermediate that can react with phosgene to produce a chlorohydroxypyrimidine. The chlorohydroxypyrimidine so produced can then react with phosgene to produce 4,6-dichloropyrimidines. If $R^1$ (see FIG. 2) is a hydrogen atom, the method of the invention produces 4,6-dichloropyrimidine itself. If $R^1$ is other than hydrogen, the method of the invention produces 5-substituted-4,6-dichloropyrimidines. For example, if $R^1$ is $CH_2CH_3$, the method of the invention produces 5-ethyl-4,6-dichloropyrimidine. The formation of chlorinated pyrimidines by cross-condensation of two different imidoyl chloride compounds according to the methods disclosed herein were unknown at the time of the present invention.

In a first aspect of the invention, the method of synthesis of chlorinated pyrimidines includes synthesis of two distinct imidoyl chloride compounds by reacting two distinct organic amides with $COCl_2$, followed by cross-condensation of the two imidoyl chloride compounds in the presence of phosgene to form the desired chlorinated pyrimidine. Organic amides are generally represented by the formula R—$CONH_2$. R can be hydrogen or a hydrocarbyl group, but is preferably hydrogen or a substituted or unsubstituted, linear or branched alkyl group, and one of the imidoyl chlorides has at least two alpha hydrogens. The general reaction for this embodiment of the invention is depicted schematically in FIG. 2 in which $R^1$ is chosen from among the $R^1$ groups disclosed above. In a preferred embodiment, the organic amides are unsubstituted alkylamides.

In a preferred embodiment of this aspect of the present invention, a first organic amide is first reacted with phosgene. In certain embodiments of this aspect of the invention, the reaction is allowed to proceed only briefly before additional reactants are added to the reaction mixture. In these certain embodiments, little or no detectable product is produced before additional reactants are added. In other embodiments of this aspect of the invention, the reaction is allowed to proceed until a substantial detectable amount of intermediate product is formed before additional reactants are added.

Once the first organic amide has reacted with phosgene to the extent desired, a second organic amide, which is a different organic amide than the first organic amide, is added to the reaction mixture. The reactants are permitted to react for a sufficient time to produce 4-chloro-6-hydroxypyrimidines and 4,6-dichloropyrimidines if sufficient phosgene is present. In certain embodiments, the reaction is allowed to proceed until a substantial detectable amount of 4,6-dichloropyrimidine is formed before the reaction is terminated.

In another embodiment of the present invention, a first organic amide is reacted with phosgene to completion (i.e., to the point where all, or essentially all, of one or more of the reactants is used up) in a first reaction vessel. Similarly, a second organic amide, which may be different than the first organic amide, is reacted with phosgene to completion in a second reaction vessel. Upon completion of the respective reactions, the two reaction mixtures are combined to form a third reaction mixture. The reacting compounds in the third reaction mixture are permitted to react for a sufficient time to produce 4-chloro-6-hydroxypyrimidines and 4,6-dichloropyrimidines if sufficient phosgene is used. In certain embodiments, the reaction is allowed to proceed until a substantial detectable amount of 4,6-dichloropyrimidine is formed before the reaction is terminated.

In yet another embodiment, a first and a second organic amide are combined to form a first mixture containing reactants. Phosgene is added to the first mixture to form a second mixture, and the mixture is reacted until 4-chloro-6-hydroxypyrimidine or 4,6-dichloropyrimidine (if enough phosgene is used) is synthesized.

In a preferred embodiment of this aspect of the invention, the two organic amides are formamide and acetamide. Formamide and acetamide are reacted, separately or together, with phosgene to form imidoyl chloride compounds, which are then converted to 4,6-dichloropyrimidine by reaction with phosgene. A general reaction scheme that accounts for the formation of 4,6-dichloropyrimidine from formamide and acetamide ($R^1$=H) is presented in FIG. 2. In this reaction mechanism, formamide and acetamide are reacted, either partially or wholly, with phosgene to produce imidoyl chloride intermediates. These imidoyl chloride intermediates condense to form an intermediate that can react with phosgene to form chlorohydroxypyrimidine. Chlorohydroxy-pyrimidine then reacts with phosgene to produce 4,6-dichloropyrimidine, carbon dioxide ($CO_2$), and hydrogen chloride (HCl).

In a second aspect of the invention, the method of synthesis of chlorinated pyrimidines includes reacting two distinct organic nitrile compounds of formula R—CN with hydrogen chloride to form two distinct imidoyl chloride compounds, which are then converted to the desired chlorinated pyrimidines by cross-condensation in the presence of phosgene. R can be a hydrogen or a hydrocarbyl group, but is preferably hydrogen or a substituted or unsubstituted, linear or branched alkyl group, preferably with less than 8 carbons, provided that one of the nitrile compounds must have 2 alpha hydrogens, for example, butyronitrile. The general reaction for this embodiment of the invention is depicted schematically in FIG. 2 in which $R^1$ is chosen from among the $R^1$ groups disclosed above. In preferred embodiments, the organic nitrites are unsubstituted alkyl nitrites.

In a third aspect of the invention, the method of synthesis of chlorinated pyrimidines includes reacting a distinct organic nitrile compound of formula R—CN with hydrogen chloride to form a distinct imidoyl chloride compound, which is cross-condensed with formamidoyl chloride (produced by the reaction of formamide and phosgene) in the presence of phosgene to produce the desired chlorinated pyrimidines. R can be a hydrogen or a hydrocarbyl group, but is preferably hydrogen or a substituted or unsubstituted, linear or branched alkyl group, preferably with less than 8 carbons, provided that the nitrile compound has 2 alpha hydrogens, for example, butyronitrile. In preferred embodiments, the organic nitrile is an unsubstituted alkyl nitrile.

In a fourth aspect of the invention, the method of synthesis of chlorinated pyrimidines includes reacting a distinct organic amide compound of formula R—$CONH_2$ with phosgene to form a distinct imidoyl chloride compound, which is cross-condensed with formamidoyl chloride (produced by the reaction of hydrogen chloride and hydrogen cyanide) in the presence of phosgene to produce the desired chlorinated pyrimidines. R can be a hydrogen or a hydrocarbyl group, but is preferably hydrogen or a substituted or unsubstituted, linear or branched alkyl group, preferably with less than 8 carbons, provided that the amide compound has 2 alpha hydrogens, for example, butyramide. In preferred embodiments, the organic amide is an unsubstituted alkyl amide.

The following examples are to illustrate the invention, but should not be interpreted as a limitation thereon.

EXAMPLES

Example 1

General Procedure for Synthesis of 4,6-dichloropyrimidine from Amides and Nitrites A Hastelloy C accelerating rate calorimetry (ARC) sphere is charged with reactants and attached to the ARC. The mixture is heated under autogenous pressure. A pressure transducer is used to monitor the pressure in the ARC sphere during the course of synthesis. After the desired reaction time, the ARC sphere is allowed to cool to room temperature (approximately 20° C.–25° C.). The residual pressure on the sphere is then vented through a caustic scrubber. Analysis of the products of the reactions is performed using liquid chromatography (LC) and gas chromatography/mass spectroscopy (GC/MS). Presence of 4,6-dichloropyrimidine in the reaction products is confirmed by comparison of the LC and GC/MS results with LC and GC/MS results obtained from an authentic sample of 4,6-dichloropyrimidine.

Liquid Chromatography Method for Analysis of 4,6-Dichloropyrimidine
Liquid Chromatograph: Hewlett-Packard 1100 liquid chromatograph with a diode array detector. Hewlett-Packard Chemstation 3D data analysis software.
Chromatography Column: Column=Highchrom HIRPB-250A;
Packing=Highchrom RPB; Length=25 cm; i.d.=4.6 mm.
HP 1100 Quaternary Pump:
Control: Flow=1.500 ml/min; Stop Time=23.00 min; Post Time=3.00 min Solvents:

Solvent A: 20.0% (20% THF, 80% ACN)
Solvent B: 80.0% (.5% $H_3PO_4$ in $H_2O$)
Solvent C: Off
Solvent D: Off Timetable

| Time | Solv.B | Solv.C | Solv.D | Flow | Pressure |
|---|---|---|---|---|---|
| 0.00 | 80.0 | 0.0 | 0.0 | 1.500 | 400 |
| 13.00 | 80.0 | 0.0 | 0.0 | 1.500 | 400 |
| 14.00 | 1.0 | 0.0 | 0.0 | 1.500 | 400 |
| 17.00 | 1.0 | 0.0 | 0.0 | 1.500 | 400 |
| 18.00 | 80.0 | 0.0 | 0.0 | 1.500 | 400 |
| 23.00 | 80.0 | 0.0 | 0.0 | 1.500 | 400 |

HP 1100 Diode Array Detector:

| | Signals | | |
|---|---|---|---|
| Signal | Store | Signal,Bw | Reference,Bw [nm] |
| A: | Yes | 250, 100 | 360, 100 |

| Retention Times: | |
|---|---|
| 2.87 minutes | 4-chloro-6-hydroxypyrimidine |
| 10.80 minutes | 4,6-dichloropyrimidine |

Gas Chromatography/Mass Spectrometry Method for Analysis of 4,6-Dichloropyrimidine
Gas Chromatograph: Hewlett-Packard 6890 gas chromatograph with a mass spectrometer detector. Hewlett-Packard Chemstation data analysis software.
Chromatography Column: Column=HP-5MS; Packing=Crosslinked 5% PH ME Siloxane; Length=30 m; i.d.=0.25 mm; 0.25 micrometer film thickness.
Oven Conditions: Initial Temperature=75° C.; Initial Time=1.00 minute; Ramp Rate=25° C. per minute; Final Temperature=290° C.; Final Time=4.00 minutes; Post Time=0.00 minutes; Run Time=13.60 minutes.
Inlet Conditions: Mode=splitless; Initial Temperature=250° C.; Pressure=8.8 psi; Purge Flow=50.0 mL/min; Purge Time=1.50 mL/min; Total Flow=53.8 mL/min; Gas Saver=On; Saver Flow=20.0 mL/min; Saver Time=3.00 min; Gas Type=Helium.
Column Conditions: Mode=Constant Flow; Initial Flow=1.0 mL/min; Nominal Initial Pressure=8.8 psi; Average Velocity=58 cm/sec; Outlet Pressure=vacuum.
Mass Spectrometer Conditions: Solvent Delay=3.00 minutes; EM Absolute=False; EM Offset=0; Resulting EM Voltage=2176.5; Low Mass=50; High Mass=550; Threshold=500; Sample #=3; MS Quad=150° C.; MS Source=230° C.
4,6-Dichloropyrimidine: Retention Time=3.27 minutes; m/e=148, 113, 86.
This general procedure was used in Examples 2–8, unless otherwise indicated.

Example 2

Synthesis of 4,6-dichloropyrimidine from Formamide and Acetamide 0.001952 moles of formamide and 0.001947 moles of acetamide were mixed together with a solution of 0.007449 moles of phosgene in 4.2 grams chlorobenzene in an ARC sphere. The sphere was then attached to the ARC and the mixture was heated to 105° C. under autogenous pressure. The above reactants were permitted to react for 100 minutes at a maximum pressure of 250 psia. The formation of 4,6-dichloropyrimdine was confirmed by LC and GC/MS.

Example 3

Synthesis of 4,6-dichloropyrimidine from Formamide and Acetamide 0.000886 moles of formamide and 0.002979 moles of acetamide were mixed together with a solution of 0.007448 moles of phosgene in 4.2 grams chlorobenzene in an ARC sphere. The sphere was then attached to the ARC and the mixture was heated to 75° C. under autogenous pressure. The above reactants were permitted to react for 1390 minutes at a maximum pressure of 95 psia. The formation of 4,6-dichloropyrimdine was confirmed by LC and GC/MS.

Example 4

Synthesis of 4,6-dichloropyrimidine from Formamide and Acetamide 0.00248 moles of formamide and 0.00206 moles of acetamide were mixed together with a solution of 0.0078 moles of phosgene in 4.4 grams chlorobenzene in an ARC sphere. The sphere was then attached to the ARC and the mixture was heated to 105° C. under autogenous pressure. The above reactants were permitted to react for 1200 minutes at a maximum pressure of 268 psia. The formation of 4,6-dichloropyrimdine was confirmed by LC and GC/MS.

Example 5

Synthesis of 4,6-dichloropyrimidine from Formamide and Acetamide 0.00228 moles of formamide and 0.00235 moles of acetamide were mixed together with a solution of 0.008436 moles of phosgene in 4.2 grams chlorobenzene in an ARC sphere. The sphere was then attached to the ARC and the mixture was heated to 105° C. under autogenous pressure. The above reactants were permitted to react for 1080 minutes at a maximum pressure of 340 psia. The formation of 4,6-dichloropyrimdine was confirmed by LC and GC/MS.

Example 6

Synthesis of 4,6-dichloropyrimidine from Formamide and Acetamide 0.003248 moles of formamide and 0.001153 moles of acetamide were mixed together with a solution of 0.008631 moles of phosgene in 4.8 grams chlorobenzene in an ARC sphere. The sphere was then attached to the ARC and the mixture was heated to 105° C. under autogenous pressure. The above reactants were permitted to react for 1110 minutes at a maximum pressure of 280 psia. The formation of 4,6-dichloropyrimdine was confirmed by LC and GC/MS.

Example 7

Synthesis of 4,6-dichloropyrimidine from Formamide and Acetonitrile/HCl 0.00255 moles of formamide and 0.18 grams of acetonitrile/HCl were mixed together with a solution of 0.00795 moles of phosgene in 4.5 grams chlorobenzene in an ARC sphere. The sphere was then attached to the ARC and the mixture was heated to 105° C. under autogenous pressure. The above reactants were permitted to react for 1410 minutes at a maximum pressure of 227 psia. The formation of 4,6-dichloropyrimdine was confirmed by LC and GC/MS.

Example 8

Synthesis of 4,6-dichloropyrimidine from Formamide Hydrochloride and Acetamide Hydrochloride 0.00123 moles of formamide hydrochloride and 0.00109 moles of acetamide hydrochloride were mixed together with a solution of 0.00869 moles of phosgene in 4.9 grams chlorobenzene in an ARC sphere. The sphere was then attached to the ARC and the mixture was heated to 105° C. under autogenous pressure. The above reactants were permitted to react for 5400 minutes at a maximum pressure of 290 psia. The formation of 4,6-dichloropyrimdine was confirmed by LC and GC/MS.

Example 9

Synthesis of 4,6-dichloropyrimidine from Acetonitrile and Formamide 0.002021 moles of formamide were mixed together with a solution of 0.005874 moles of phosgene in 3.1 grams acetonitrile in an ARC sphere. The sphere was then attached to the ARC and the mixture was heated to 105° C. under autogenous pressure. The above reactants were permitted to react for 180 minutes at a maximum pressure of 162 psia. The formation of 4,6-dichloropyrimdine was confirmed by LC and GC/MS.

Example 10

Synthesis of 4,6-dichloropyrimidine from Acetonitrile and Formamide 0.000735 moles of formamide were mixed together with a solution of 0.005874 moles of phosgene in 3.1 grams acetonitrile in an ARC sphere. The sphere was then attached to the ARC and the mixture was heated to 105° C. under autogenous pressure. The above reactants were permitted to react for 180 minutes at a maximum pressure of 116 psia. The formation of 4,6-dichloropyrimdine was confirmed by LC and GC/MS.

Example 11

Synthesis of 5-ethyl-4,6-dichloropyrimidine from Butyronitrile and Formamide 0.00196 moles of formamide were mixed together with a solution of 0.005881 moles of phosgene in 3.1 grams butyronitrile in an ARC sphere. The sphere was then attached to the ARC and the mixture was heated to 105° C. under autogenous pressure. The above reactants were permitted to react for 180 minutes at a maximum pressure of 140 psia. The formation of 5-ethyl-4,6-dichloropyrimdine was confirmed by LC and GC/MS.

It will be apparent to those skilled in the art that various modifications and variations can be made in the practice of this invention without departing from the scope or spirit of the invention. Other embodiments of the invention will be apparent to those skilled in the art from consideration of the specification and practice of the invention disclosed herein. It is intended that the true scope and spirit of the invention is indicated by the following claims. All references cited herein are hereby incorporated by reference in their entireties.

What is claimed is:

1. A method of synthesizing 4,6-dichioropyrimidine, 5-substituted-4,6-dichloropyrimidines, 4-chloro-6- hydroxypyrimidine, or 5-substituted-4-chloro-6-hydroxypyrimidines, said method comprising reacting a first imidoyl chloride compound which is formamidoyl chloride and a second imidoyl chloride compound with phosgene, wherein the second imidoyl chloride compound has two alpha hydrogens and said imidoyl compounds are represented by the formulas:

in which $R^1$ is selected from hydrogen and a $C_1$–$C_{12}$ hydrocarbyl group.

2. The method of claim 1, wherein $R^1$ is hydrogen.

3. The method of claim 1, wherein $R^1$ is a $C_1$–$C_3$ alkyl group.

4. The method of claim 1, wherein $R^1$ is methyl.

5. The method of claim 1, further comprising synthesizing said first imidoyl chloride compound and said second imidoyl chloride compound by reaction of:
   a) at least one organic amide of structure R—$CONH_2$ with phosgene, or
   b) at least one organic nitrile of structure R—CN with hydrogen chloride, or
   c) both at least one organic amide of structure R—$CONH_2$ with phosgene and at least one organic nitrile of structure R—CN with hydrogen chloride; wherein each R group is, independently, hydrogen or a $C_1$–$C_{12}$ hydrocarbyl group.

6. The method of claim 5, wherein said group R is a substituted or unsubstituted, linear or branched alkyl group.

7. The method of claim 5, wherein one organic nitrile is butyronitrile.

8. The method of claim 5, wherein one organic nitrile is acetonitrile.

9. The method of claim 5, wherein said first imidoyl chloride compound is synthesized by reacting formamide with phosgene, and said second imidoyl chloride compound is synthesized by reacting acetamide with phosgene.

10. The method of claim 5, wherein said first imidoyl chloride compound is synthesized by reacting hydrogen cyanide with hydrogen chloride, and said second imidoyl chloride compound is synthesized by reacting acetonitrile with hydrogen chloride.

11. The method of claim 5, wherein said first imidoyl chloride compound is synthesized by reacting formamide with phosgene, and said second imidoyl chloride compound is synthesized by reacting acetonitrile with hydrogen chloride.

12. The method of claim 5, wherein said first imidoyl chloride compound is synthesized by reacting formamide with phosgene, and said second imidoyl chloride compound is synthesized by reacting butyronitrile with hydrogen chloride.

13. The method of claim 5, wherein the process is carried out in an inert organic solvent.

14. The method of claim 5, wherein the process is carried out in an excess of nitrile.

15. The method of claim 5, wherein the process is carried out in an excess of phosgene.

16. The method of claim 5, wherein the process is carried out in an excess of amide.

17. The method of claim 5, wherein the process is carried out in stages with the formation of imidoyl chlorides, either separately or as a mixture, being done and then a mixture of the imidoyl chlorides is treated with phosgene to generate the products.

18. The method of claim 5, wherein the process is carried out in one stage with the formation of imidoyl chlorides being done concurrently with treatment by phosgene to generate the products.

19. The method of claim 5, wherein the process is carried out with continuous feed of raw materials into a reactor system and outflow and recovery of product.

20. The method of claim 5, wherein the process is carried out in batches with discreet steps for charging raw materials and recovery of product.

21. The method of claim 5, wherein the process is carried out at 0° C. to 300° C.

22. The method of claim 5, wherein the process is carried out at 60° C. to 160° C.

23. The method of claim 5, wherein the process is carried out at 80° C. to 130° C.

24. The method of claim 5, wherein the process is carried out at pressures of 0 to 800 psig.

25. The method of claim 5, wherein the process is carried out at pressures of 100 to 300 psig.

26. The method of claim 5, wherein the process is carried out at pressures of 150 to 250 psig.

* * * * *